United States Patent
Golubovic-Liakopoulos et al.

(10) Patent No.: US 7,560,036 B2
(45) Date of Patent: Jul. 14, 2009

(54) SYSTEM AND METHOD FOR DRUG DELIVERY AND MICROFLUIDIC APPLICATIONS USING MICRONEEDLES

(75) Inventors: Nevenka Golubovic-Liakopoulos, Bridgewater, NJ (US); Glenn Fricano, Great River, NY (US); Michael Danielson, Wrentham, MA (US)

(73) Assignee: Apogee Technology, Inc., Norwood, MA (US)

( * ) Notice: Subject to any disclaimer, the term of this patent is extended or adjusted under 35 U.S.C. 154(b) by 9 days.

(21) Appl. No.: 11/133,245

(22) Filed: May 20, 2005

(65) Prior Publication Data

US 2006/0030812 A1      Feb. 9, 2006

Related U.S. Application Data

(60) Provisional application No. 60/598,831, filed on Aug. 5, 2004.

(51) Int. Cl.
  *A61B 17/20*      (2006.01)
(52) U.S. Cl. .............................. 216/2; 216/11; 216/99; 438/398; 604/46; 604/173
(58) Field of Classification Search ........................ None
  See application file for complete search history.

(56) References Cited

U.S. PATENT DOCUMENTS

| | | | |
|---|---|---|---|
| 6,312,612 B1 * | 11/2001 | Sherman et al. ................. 216/2 |
| 6,379,324 B1 * | 4/2002 | Gartstein et al. ............... 604/22 |
| 6,406,638 B1 | 6/2002 | Stoeber et al. | |
| 6,533,949 B1 | 3/2003 | Yeshurun et al. | |
| 6,558,361 B1 | 5/2003 | Yeshurun | |
| 6,589,202 B1 | 7/2003 | Powell | |
| 6,591,124 B2 | 7/2003 | Sherman et al. | |
| 6,611,707 B1 | 8/2003 | Prausnitz et al. | |
| 6,652,478 B1 | 11/2003 | Gartstein et al. | |
| 6,689,100 B2 | 2/2004 | Connelly et al. | |
| 6,767,341 B2 | 7/2004 | Cho | |

(Continued)

FOREIGN PATENT DOCUMENTS

WO    WO 2003015860 A1  *  2/2003

OTHER PUBLICATIONS

William Leventon, "New Coatings and Processes Add Value to Medical Devices", published by Medical Device & Diagonistic Industry, MDDI Aug. 2001.

(Continued)

*Primary Examiner*—Allan Olsen
(74) *Attorney, Agent, or Firm*—Elliot M. Olstein; Raymond J. Lillie

(57) ABSTRACT

The invention relates to a method of fabricating a microneedle array in a substrate, a drug delivery device comprising one or more microneedles extending upwards from the front surface of the substrate, the microneedles having a generally conical-shaped body defined by a plurality of surfaces sloping upwards from a relatively broad base to a tip, and one or more substances coating the microneedles, the one or more substances being operable to be administered to a patient, wherein the tips of the one or more microneedles are sufficiently sharp to penetrate an outer layer of the skin of the patient, and a method of administering one or more substances to a patient using the device.

43 Claims, 13 Drawing Sheets

U.S. PATENT DOCUMENTS

| | | | |
|---|---|---|---|
| 6,790,372 B2 * | 9/2004 | Roy et al. .................... 216/10 |
| 2002/0082543 A1 * | 6/2002 | Park et al. .................... 604/21 |
| 2003/0045837 A1 | 3/2003 | Delmore et al. |
| 2003/0135161 A1 | 7/2003 | Fleming et al. |
| 2004/0267205 A1 * | 12/2004 | Stemme et al. ............ 604/173 |
| 2005/0171480 A1 * | 8/2005 | Mukerjee et al. ........... 604/173 |
| 2006/0084942 A1 * | 4/2006 | Kim et al. ............... 604/890.1 |

OTHER PUBLICATIONS

Lonny Wolgemuth, "Assessing the Performance and Suitability of Parylene Coating", published by Medical Device & Diagnostic Industry Magazine MDDI Article Index, Aug. 2000.

Ranit Mishori, "Special Delivery", The Washington Post, Feb. 8, 2005; p. HE01.

International Search Report mailed Jul. 21, 2006; International Application No. PCT/US05/17627.

\* cited by examiner

SYSTEM AND METHOD FOR DRUG DELIVERY AND MICROFLUIDIC APPLICATIONS USING MICRONEEDLES

RELATED APPLICATION DATA

This application claims benefit of priority of Provisional Application Ser. No. 60/598,831 filed on Aug. 5, 2004 entitled "ANISOTROPICALLY ETCHED NEEDLES FOR MICROFLUIDIC APPLICATIONS", the entire disclosure of which is incorporated herein by reference.

FIELD OF THE INVENTION

This invention relates to a system and method for drug delivery and other microfluidic applications using microneedles. More specifically, this invention relates to a system and method for delivering substances under a patient's skin using anisotropically etched microneedles in a substrate and a method of making the microneedles.

BACKGROUND OF THE INVENTION

Transdermal drug delivery (TDD) is a non-invasive, convenient and painless dosage form which offers numerous clinical benefits such as steady blood-level profile, reduced systemic side effects, and often an improved efficacy and patient compliance. But TDD is not clinically justified for all drugs and is currently a limited technology suitable for a niche set of drugs. Current innovations in TDD mostly occur in system and formulation solutions, where system innovations refer to various approaches to increasing drug flux across the skin. Stratum corneum, the outermost layer of the skin, prevents passive permeability of most compounds including drugs, except for those of low molecular weight and lipophilic. Therefore, it is impossible to transdermally deliver proteins, vaccines and most biopharmaceuticals, without a chemical or physical method of enhancing the passive diffusion mechanism.

Much research has been going on in developing transdermal technologies that utilize mechanical energy to increase drug flux across the skin, such as iontophoresis, sonophoresis, electroporation and thermal energy. Another area of research is in creation of micropores in stratum corneum to provide a path of lower resistance to diffusion of drug molecules. These devices include microstructures, usually referred to as microneedles, (also referred to as microprojections, microtips, etc.), made of various materials such as metal, PMMA, glass, silicon, etc.

Some advantages of silicon based microneedles lie in that they are realized using traditional CMOS processing techniques, which makes them suitable for integration with other components to facilitate added functionality (iontophoresis, thermal components, etc.). A limitation of known microneedles lies in the complexity of known manufacturing processes, which results in long and challenging product development, and often requires specialty tools. This ultimately results in low yield manufacturing process, lack of reproducibility and high cost.

Many existing methods and systems for drug delivery include microneedles to break the skin as the barrier and to enhance passive diffusion of drugs across the stratum corneum. Fundamentally, these systems typically incorporate microneedles for micropore formation, but technologically vary in how the microneedles are realized, and in how drug is delivered into the patient. For example, U.S. Pat. No. 6,767,341 issued to Cho describes an array of hollow microneedles fabricated in a silicon substrate using conventional semiconductor manufacturing methods.

Alignment of the hole to the microneedle is another limiting factor. Typically, back-to-front alignment allows for greater than 5 microns tolerance, which results in a large error when attempting to precisely place the hole on a side of the microneedle. Forming the hole through a microneedle additionally compromises the mechanical robustness of the microneedle, which represents a significant issue because the microneedles must ultimately penetrate into the patient, and it is unacceptable for microneedles to break inside the patient and remain inside the patient's body. In addition, microfluidic components are often required for complete drug delivery solutions. From the silicon processing and system integration standpoint, this becomes a highly involved manufacturing process and consequently not a high volume/high yield, low cost scenario, and existing systems thus lack economical viability.

U.S. Pat. No. 6,689,101 issued to Connelly et al. relates to a variety of devices that incorporate microneedles realized using different processing techniques in a variety of materials. The described delivery mechanism involves an array of orifices through an array of skin penetrating members and it fundamentally suffers the same drawbacks as those described in the analyses above. Similarly, U.S. Pat. No. 6,611,707 issued to Prausnitz at al. describes a substrate to which a plurality of microneedles are attached or integrated, and at least one reservoir containing the drug, which communicates with microneedles via additional microfluidic components. In addition, U.S. Pat. Nos. 6,558,361 and 6,533,949 describe methods for processing a wafer to form a plurality of hollow microneedles projecting from the substrate. Issues such as alignment, reproducibility, system complexity, reliability, throughput and cost are as present as in all above mentioned references. Also, U.S. Pat. No. 6,406,638 is another example of a microneedle design and fabrication process that does not clearly exhibit economical viability.

Thus, there is a need for microneedles which can be produced in a precise and economically viable manner while achieving suitable robustness for intradermal delivery of substances.

SUMMARY OF THE INVENTION

The invention relates to a system and method for delivering drugs intradermally using anisotropically etched MEMS microneedles in silicon. In particular, the invention provides microneedles which are fabricated in a crystal silicon material suitable for use in the administration of vaccines and all systemic drugs and which reduce the dosage needed and patient discomfort during injection. In addition, the invention provides an economically viable method of producing multiple arrays of microneedles and an economically and clinically viable method of intradermally delivering drugs into the patient's body. Furthermore, the invention provides a method of creating and coating microneedles. Moreover, the invention provides a concept of penetrating the skin using drug coated microneedles, followed by release of the coating into the patient's body using a physiological fluid as a swelling mechanism, followed by a timed release of the drug into the patient's circulatory system. Thus, the invention eliminates the need for complex microfluidic components.

In addition, the invention relates to a drug delivery device for administration of various drugs intradermally, including large molecules such as proteins, biopharmaceuticals, etc. The invention employs drug diffusion, microporation of the stratum corneum, and polymer-drug deposition within the patient's skin and subsequent dissolution. Micropores are made into the stratum corneum by means of a microneedle array penetration, which can optionally be further enhanced by applying ultrasonic and/or electric signals across or through the skin.

An embodiment of the invention relates to a method of fabricating a microneedle array in a substrate having a front surface and a back surface, the method comprising the steps of forming one or more protective layers on the front surface of the substrate, removing at least a portion of the one or more protective layers, removing the photoresist, and anisotropically etching the front surface of the substrate to create one or more microneedles that extend upwards from the substrate, the microneedles having a generally conical-shaped body defined by a plurality of surfaces sloping upwards from a relatively broad base to a tip, wherein the bases of the one or more microneedles are integrally formed of the substrate and the tips are sufficiently sharp to penetrate an outer layer of the skin of a patient. Furthermore, an offset portion may be formed in the substrate.

In addition, an embodiment of the invention relates to a drug delivery device comprising a substrate having a back surface and a front surface, one or more microneedles extending upwards from the front surface of the substrate, the microneedles having a generally conical-shaped body defined by a plurality of surfaces sloping upwards from a relatively broad base to a tip, and one or more substances coating the microneedles, the one or more substances being operable to be administered to a patient, wherein the tips of the one or more microneedles are sufficiently sharp to penetrate an outer layer of the skin of the patient.

Furthermore, an embodiment of the invention relates to a method of administering one or more substances to a patient comprising the steps of penetrating at least an outer layer of the skin of the patient with one or more microneedles extending from a front surface of a substrate, at least one of the one or more microneedles being coated with one or more substances to be administered to the patient, and releasing at least one of the one or more substances into the patient, wherein the microneedles have a generally conical-shaped body defined by a plurality of surfaces sloping upwards from a relatively broad base to a tip.

Moreover, an embodiment of the invention relates to a method of administering one or more substances to a patient comprising the steps of penetrating at least an outer layer of the skin of the patient with one or more microneedles extending from a front surface of a substrate, at least one of the microneedles having one or more holes extending from a back surface of the substrate to a surface of the at least one microneedle, and transferring one or more substances from the back surface of the substrate through the one or more holes extending from the back surface of the substrate to the surface of the at least one microneedle and into the patient, wherein the microneedles have a generally conical-shaped body defined by a plurality of surfaces sloping upwards from a relatively broad base to a tip.

DETAILED DESCRIPTION OF THE DRAWINGS

Referring now to the figures, this invention relates to a system and method for drug delivery and microfluidic applications using microneedles, specifically, a system and method for delivering drugs intradermally using anisotropically etched MEMS microneedles in silicon. Micro-needles that can be readily integrated with on-board micro-fluidic components in addition to microelectronics have potential applications in the chemical and biomedical fields for localized chemical analyses, programmable drug-delivery systems as well as any precise sampling of fluids. Robust designs that can penetrate biological tissue are necessary.

FIGS. 1-7 illustrate a method of fabricating a microneedle array in a substrate 101 according to an embodiment of the invention. In general, the microneedle array is preferably fabricated in single crystal silicon by use of standard, CMOS compatible, processing techniques that consist of the following general steps: wafer cleaning, thin film deposition for protecting the wafer during wet etching, photolithography, thin film etching, anisotropic KOH etching, removal of protective thin films, and wafer dicing. Generally, any size (4, 6, 8-inch or other) single crystal silicon substrate may be used, with a 1-10 ohm/cm phosphorus doped or different doping concentration.

Figure 1:
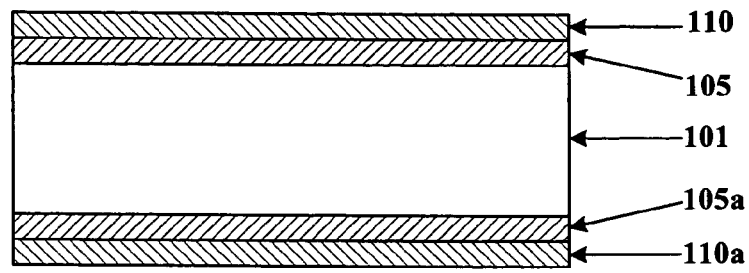
FIG. 1 shows an embodiment of the invention wherein two protective layers have been formed on a substrate.

Referring to FIG. 1, the substrate for the microneedle array is preferably a silicon wafer, more preferably a single crystal silicon wafer. Silicon is a material of choice for micro-needle realization due to its high mechanical strength and durability, biological and IC compatibility and possibility of integration with other components of a more complex micro-fluidic system. The substrate may be of any size, for example, 6-12 inches in diameter. In addition, the substrate is preferably n-type doped, with the doping concentration preferably in the range of 1-10 ohm-cm. After cleaning substrate 101, one or more protective layers 105 and 110 are formed on the front surface 102 of the substrate. If the back surface 102$a$ of substrate 101 is to be etched, one or more protective layers 105$a$ and 110$a$ may also be formed on back surface 102$a$.

Protective layers 105, 110, 105$a$, and 110$a$ may include, for example, one or more oxide layers which are grown on the surfaces of the substrate by any means known in the art, for example, by thermal oxidation, and silicon nitride layers which are deposited by any means known in the art, for example, by high quality low pressure chemical vapor deposition. If oxide layers are formed, it is preferred that a thickness of several hundred Angstroms of oxide deposit be formed. Protective layers 105, 110, 105$a$, and 110$a$ may also be formed any kind of oxide and nitride, for example, thermal, LPCVD, PECVD, and the like, and metals, for example, gold, platinum, chromium, silicon carbide, and the like. Generally, when TMAH is used as the etchant, other materials including aluminum may be used in the protective layers.

Figure 2:
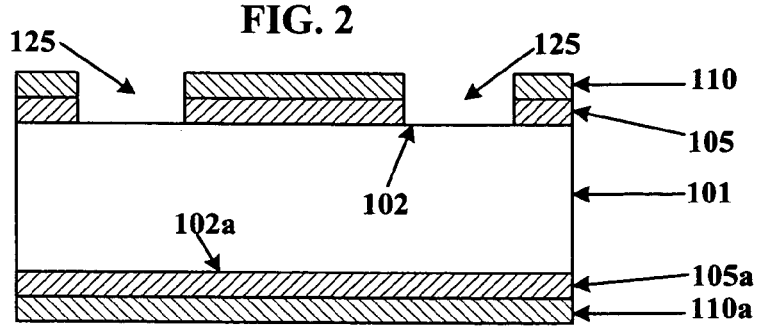
FIG. 2 shows the substrate of FIG. 1 wherein the protective layers have been etched to form a mask according to an embodiment of the invention.

After the protective layers are formed on the substrate, at least a portion of the one or more protective layers are removed to facilitate etching of the substrate. This step may include, for example, performing photolithography on the front surface of the substrate to create a footprint for the microneedle array, etching one or more of the protective layers using reactive ion etching (RIE), and removing the photoresist. In particular, standard photoresist may be spun coated onto the substrate, following exposure and development of the photosensitive film. The protective layers may then be etched using standard etching techniques, preferably reactive ion etching. The removal of the protective layers may occur one layer at a time or simultaneously. FIG. 2 shows substrate 101 after portions 125 of protective layers 105 and 110 have been removed. At this point in the method, the front surface 102 of substrate 101 is exposed.

Figure 3:
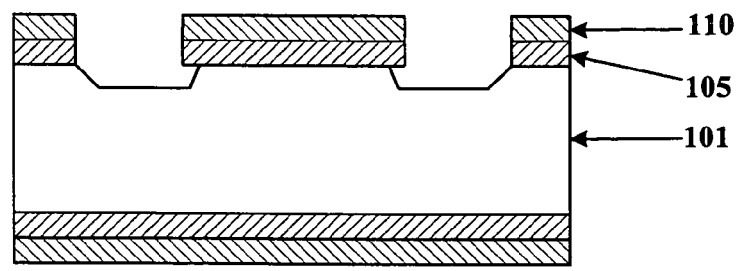
FIG. 3 shows the substrate of FIG. 2 after a first portion of the substrate is etched according to an embodiment of the invention.
Figure 4:
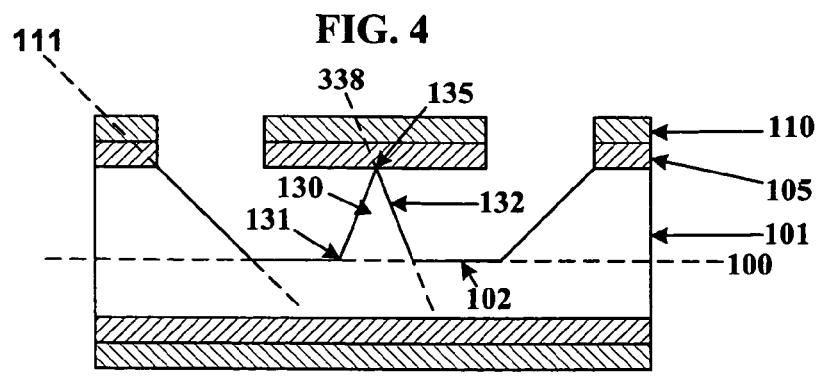
FIG. 4 shows the substrate of FIG. 3 after the substrate is further etched to form a microneedle according to an embodiment of the invention.
Figure 5:
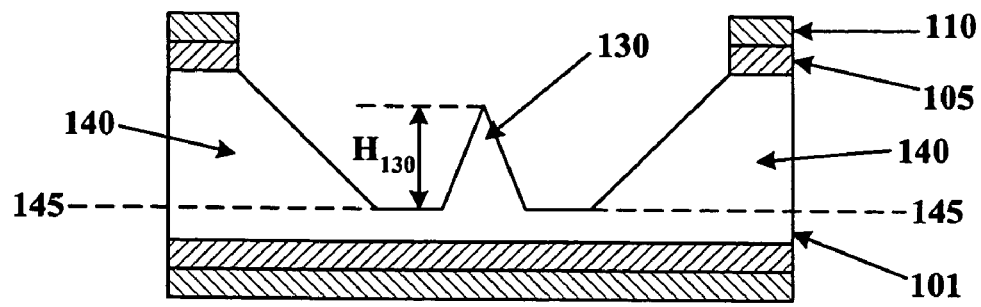
FIG. 5 shows the substrate of FIG. 4 after the etching is complete and the microneedle is formed according to an embodiment of the invention.

As is shown in FIGS. 3-5, front surface 102 of substrate 101 is then anisotropically etched to create one or more microneedles 130 that extend upwards from the front surface 102 of substrate 101. Substrate 101 may be anisotropically etched using any suitable method including, for example, RIE, KOH, TMAR (or EDP, hydrazine) in a range of solution temperatures and concentrations. Preferably, the anisotropic etch is an anisotropic timed KOH etch at an elevated temperature in the range from 40° C. to 95° C., with continuous stirring, using a reflux bath. Each microneedle 130 is preferably etched to have a generally conical-shaped body defined by a plurality of surfaces 132 sloping upwards from a relatively broad base 131 to a tip 135. Microneedle 130 intersects with substrate 101 at base 131, which is integrally formed with the substrate 101. Moreover, tip 135 of microneedle 130 is preferably sufficiently sharp to penetrate an outer layer of the skin of a patient as shown in FIG. 4. At this point, portions of protective layers 110 and 105 covering tip 132 are removed, as shown in FIG. 5. Any known removal process can be used in this step.

Figure 6:
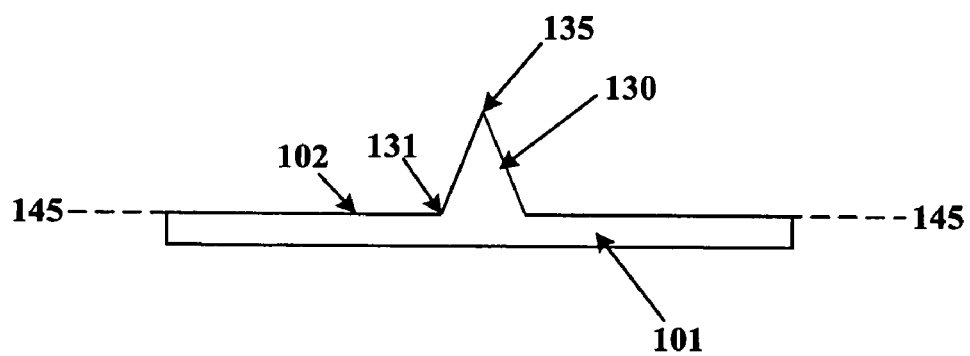
FIG. 6 shows the substrate of FIG. 5 with the microneedle extending upwards from the substrate according to an embodiment of the invention.

After microneedle 130 is anisotropically etched, at least a portion of substrate 101 located above the front surface 102 of substrate 101 immediately adjacent to base 131 of microneedle 130 is removed. As is shown in FIG. 5, the portions of substrate 101 removed in this step includes portions 140 above the plane 145 passing through the base 131 of microneedle 130. After removal, microneedle 130 is defined as shown in FIG. 6. Any known technique, such as various etching techniques can be used for the removal in this step. Thus, as is shown in FIG. 6, after this step is completed, the front surface 102 of substrate 101 is relatively level except for microneedle 130 which extend upwards from front surface 102 above plane 145. Accordingly, the tip 135 of microneedle 130 tip is the highest point on the substrate 101, while the base 131 of microneedle 130 lies on the plane of the substrate 101.

Figure 7:
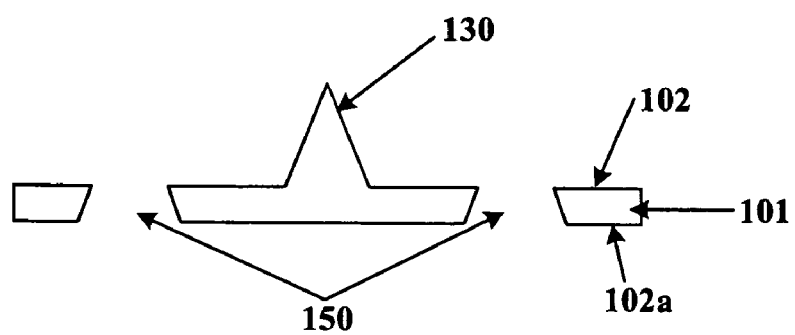
FIG. 7 shows the substrate of FIG. 6 wherein the substrate has through-holes extending from the back surface of the substrate to the front surface of the substrate according to an embodiment of the invention.
Figure 8:
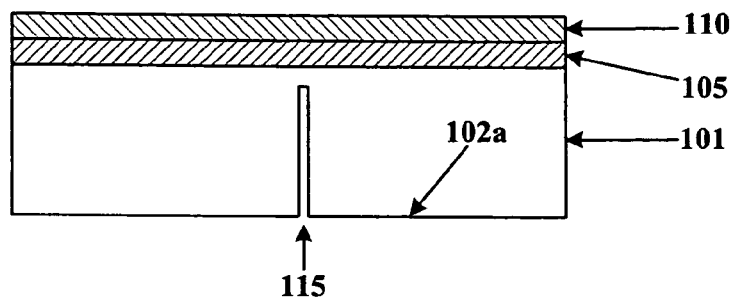
FIG. 8 shows an embodiment of the invention wherein protective layers have been grown or deposited on a substrate and a through-hole has been drilled into the substrate.
Figure 9:
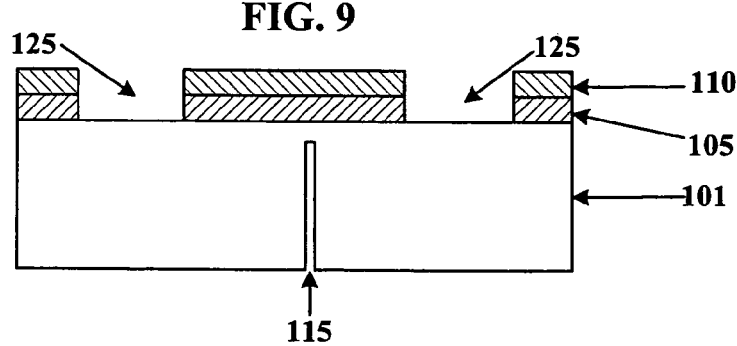
FIG. 9 shows the substrate of FIG. 8 wherein the protective layers have been etched to form a mask according to an embodiment of the invention.
Figure 10:
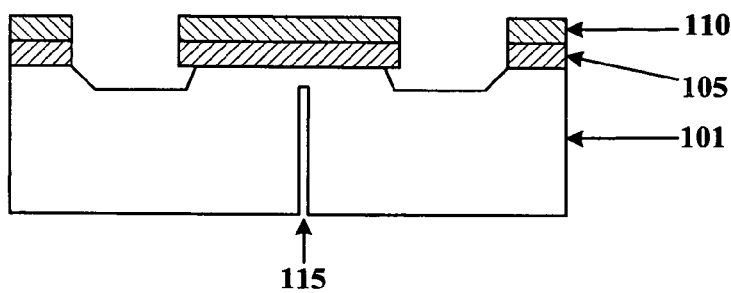
FIG. 10 shows the substrate of FIG. 9 after a first portion of the substrate is etched according to an embodiment of the invention.
Figure 11:
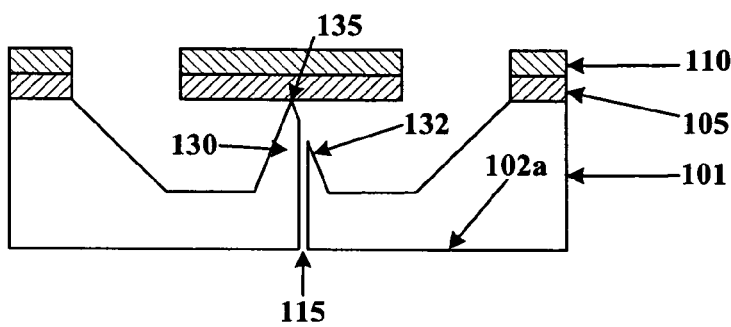
FIG. 11 shows the substrate of FIG. 10 after the substrate is further etched to form a microneedle with a through-hole according to an embodiment of the invention.
Figure 12:
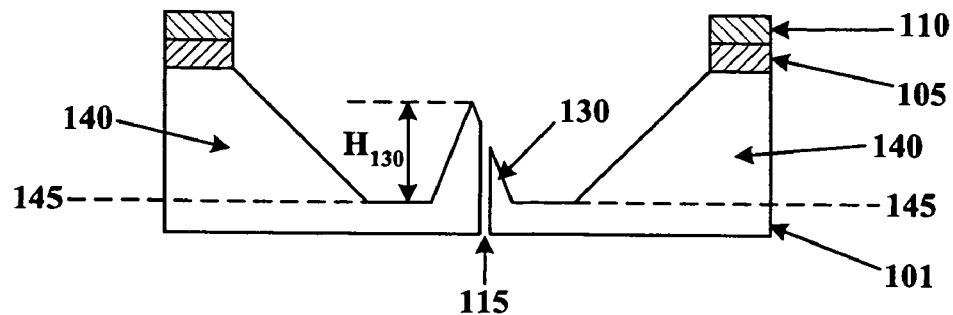
FIG. 12 shows the substrate of FIG. 11 after the etching is complete and the microneedle is formed according to an embodiment of the invention.
Figure 13:
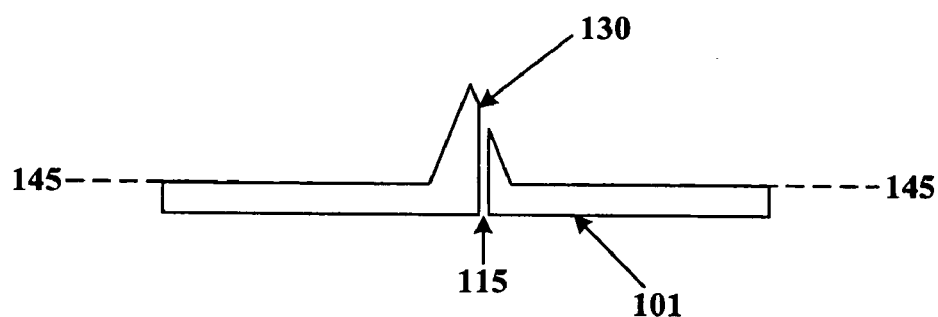
FIG. 13 shows the substrate of FIG. 12 with the microneedle extending upwards according to an embodiment of the invention.
Figure 14:
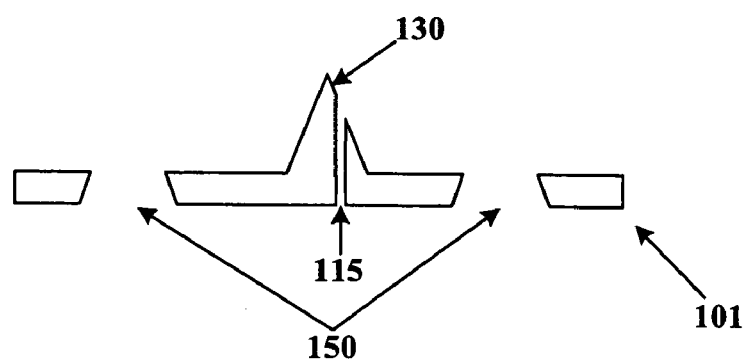
FIG. 14 shows the substrate of FIG. 13 wherein the substrate has through-holes extending from the back surface of the substrate to the front surface of the substrate according to an embodiment of the invention.
Figure 15:
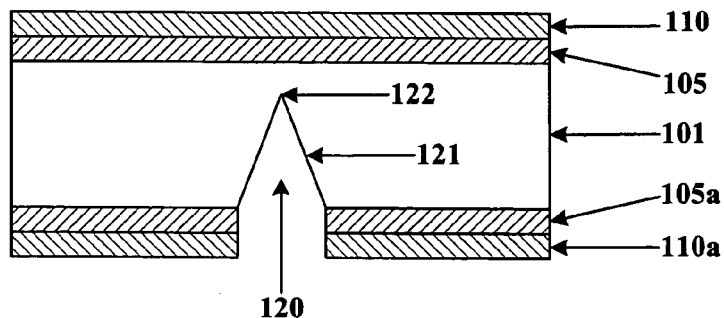
FIG. 15 shows an embodiment of the invention wherein protective layers have been grown or deposited on a substrate and a conical hole has been etched into the back surface of the substrate.
Figure 16:
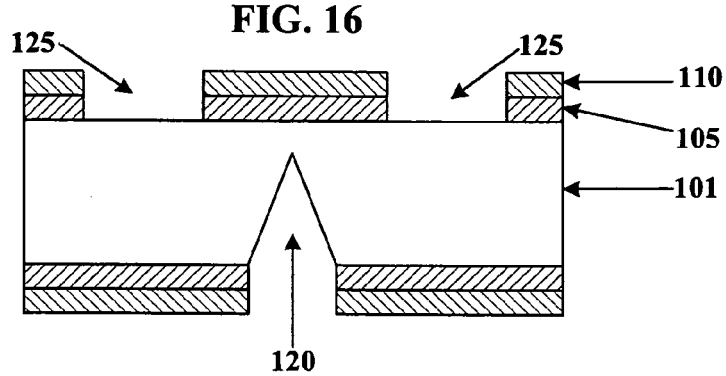
FIG. 16 shows the substrate of FIG. 15 wherein the protective layers have been etched to form a mask according to an embodiment of the invention.
Figure 17:
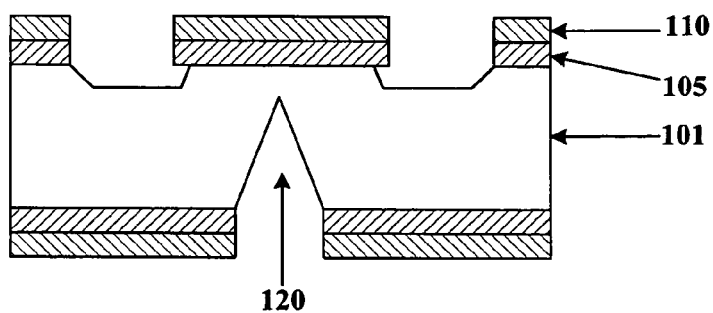
FIG. 17 shows the substrate of FIG. 16 after a first portion of the substrate is etched according to an embodiment of the invention.
Figure 18:
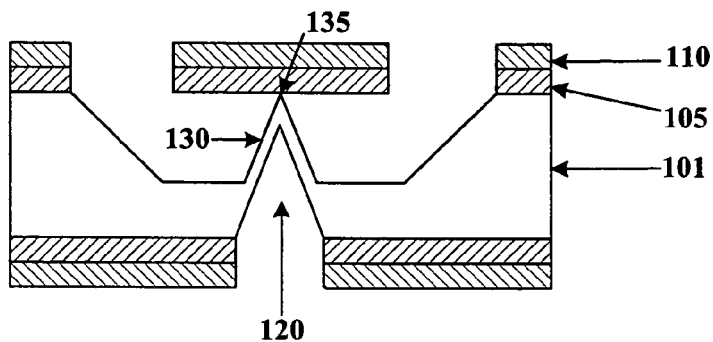
FIG. 18 shows the substrate of FIG. 17 after the substrate is further etched to form a microneedle according to an embodiment of the invention.
Figure 19:
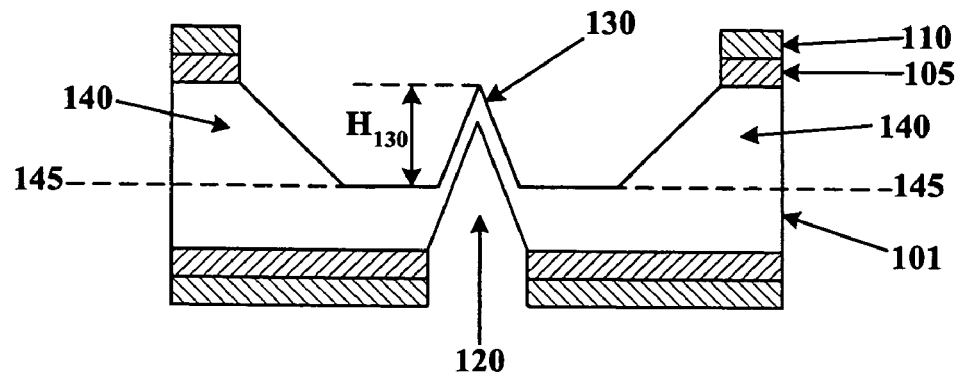
FIG. 19 shows the substrate of FIG. 18 after the etching is complete and the microneedle is formed according to an embodiment of the invention.
Figure 20:
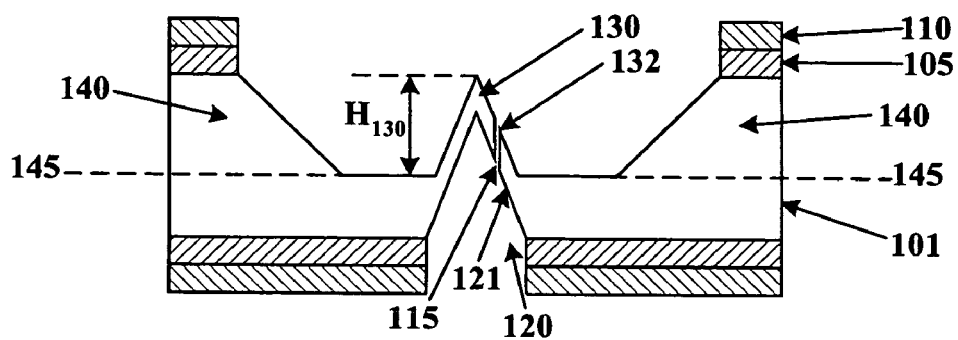
FIG. 20 shows the substrate of FIG. 19 wherein the microneedle has a through-hole according to an embodiment of the invention.

In addition, as is shown in FIG. 7, after the microneedle array is formed as described above, one or more one or more groove-shaped through-holes 150 may be formed in substrate 101 that extend from the back surface 102a of substrate 101 to the front surface 102 of substrate 101. Through-holes 150 may be formed using DRIE technique or a combination of anisotropic etching and laser drilling, focused ion beam, EDM or Coherent Porous Silicon (CPS) method. These through-holes facilitate the transfer of substances from the back side of the substrate to the front side of the substrate.

FIGS. 8-14 show an embodiment of the invention wherein one or more holes 115 extend from the back surface 102a of substrate 101 to at least one of the surfaces 132 of the one or more microneedles 130. The method for fabricating the microneedle 130 shown in these figures is substantially identical to the method described above with reference to FIGS. 1-7 with the exception that at least one of the microneedles 130 is positioned above the one or more holes 115, which is formed prior to the step of anisotropically etching substrate 101 to form microneedle 130. Hole 115 may be formed using a DRIE technique or a combination of one or more of anisotropic etching and laser drilling, focused ion beam, EDM or Coherent Porous Silicon (CPS) method. Hole 115 allows the transfer of substances, such as a drug, from the back surface 102a of the substrate 101 to the surface of the microneedles. As shown, the microneedle can be formed so that the tip thereof is offset from the hole to provide a more structurally sound microneedle and a better tip for penetration.

FIGS. 15-22 show an embodiment of the invention wherein the method for fabricating the microneedle 130 shown in these figures is also substantially identical to the method described above with reference to FIGS. 1-7. However, in this embodiment, one or more conical holes 120 are formed in the back surface 102a of the substrate 101. In particular, one or more protective layers 105a and 110a are formed on the back surface 102a of the substrate 101. As described above, protective layers 105a and 110a may include, for example, one or more oxide layers which are grown on the surfaces of the substrate by any means known in the art, for example, by thermal oxidation, and silicon nitride layers which are deposited by any means known in the art, for example, by low pressure chemical vapor deposition.

After protective layers 105a and 110a are formed on substrate 101, at least a portion of the one or more protective layers are removed to facilitate etching of the substrate to form the conical holes 120. This step may include, for example, performing photolithography on the back surface of the substrate to create a footprint for conical holes, etching one or more of the protective layers using reactive ion etching, and removing the photoresist. Next, after the back surface 102a is exposed, the back surface of the substrate is anisotropically etched to form the one or more conical holes 120 in the substrate. As described above, any suitable method may be used to etch the back surface of substrate 101 including, for example, KOH or TMAH etching (or EDP, hydrazine) in a range of solution temperatures and concentrations.

As shown in FIGS. 18-22, at least one of conical holes 120 extends from the back surface 102a of the substrate 101 into the body of the one or more microneedles 130. Thus, when the microneedles 130 are completely formed, the tip 122 of the conical holes 120 extends into the body of the microneedles 130, thus essentially making microneedles 130 hollow. In addition, each of conical holes 120 have a plurality of internal surfaces 121 formed by the etching.

Figure 21:
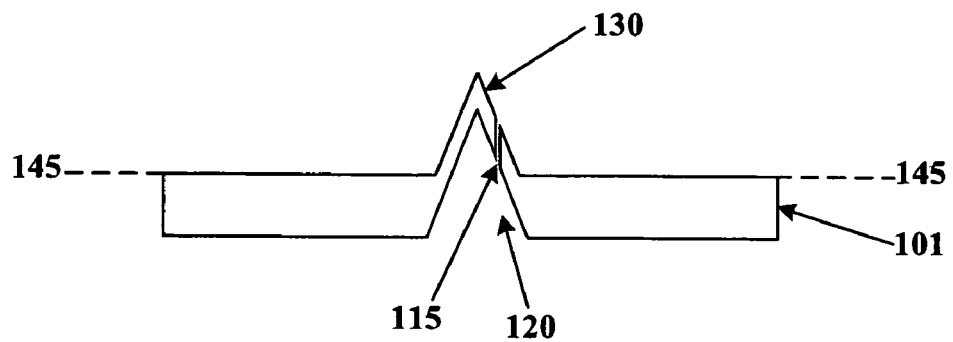
FIG. 21 shows the substrate of FIG. 20 with the microneedle extending upwards according to an embodiment of the invention.
Figure 22:
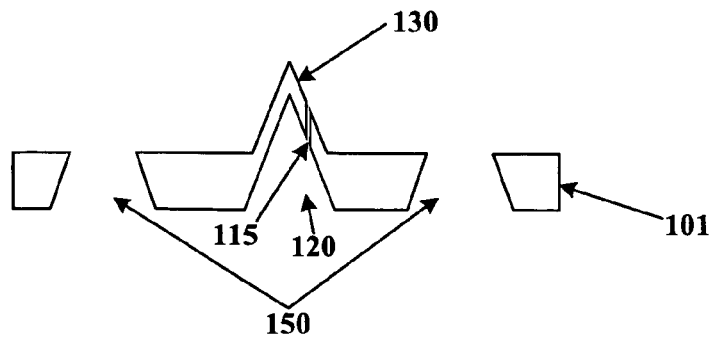
FIG. 22 shows the substrate of FIG. 21 wherein the substrate has through-holes extending from the back surface of the substrate to the front surface of the substrate according to an embodiment of the invention.

After the conical holes 120 are formed, one or more additional holes 115 are formed such that holes 115 extend through substrate 101 from at least one of the internal surfaces 121 of the one or more conical holes 120 to the surfaces 132 of the one or more microneedles 130, as illustrated in FIGS. 21 and 22. Conventional techniques can be used to form holes 115. Since the silicon defining the microneedles is very thin, formation of holes 115 is simplified.

Accordingly to another embodiment of the invention shown in FIGS. 38-43, a lateral groove 123 may be formed in substrate 101 prior to formation of the microneedles. Lateral groove 123 is a relatively long groove having internal sides 121 and a sharp tip. Lateral groove 123 is similar to conical holes 120 in that it extends into the substrate a sufficient depth (above surface 145) to enter into the portion of the substrate from which microneedle 130 is formed.

Figure 41:
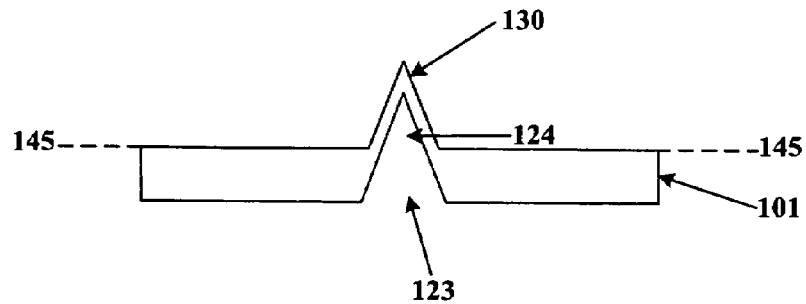
FIG. 41 shows a cross-sectional side view of a microneedle formed over a lateral groove accordingly to the embodiment shown in FIG. 38.
Figure 42:
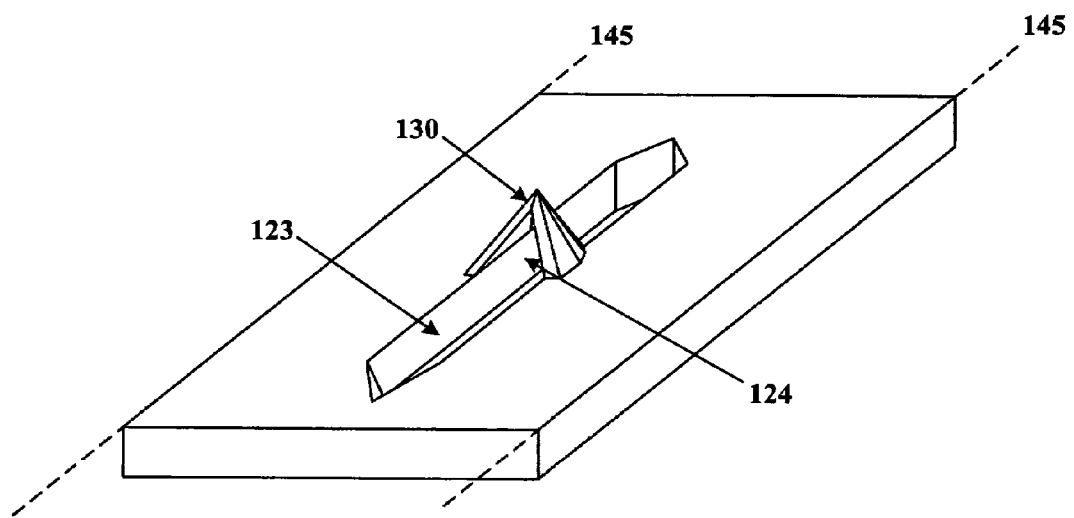
FIG. 42 shows a perspective view of a microneedle formed over a lateral groove accordingly to the embodiment shown in FIG. 38.
Figure 43:
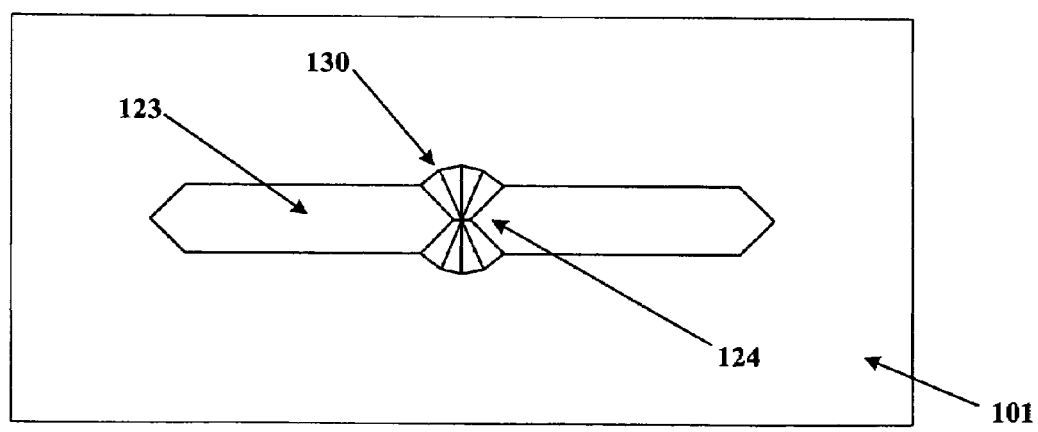
FIG. 43 shows a top view of a microneedle formed over a lateral groove accordingly to the embodiment shown in FIG. 38.

Thus, as is shown in FIG. 41, when microneedle 130 is formed, the tip of lateral groove 123 is within the body of the microneedle. In addition, the shape of lateral groove 123 also creates an opening 124 on the sides of microneedle 130. As is shown in FIGS. 42-43, opening 124 is present on both sides of microneedle 130, the size of which can be controlled by the depth of lateral groove 123 in substrate 101. In particular, the deeper lateral groove 123 extends into microneedle 130, the larger opening 124 will be. Thus, lateral groove 123 provides an easily-controlled channel from the back of substrate 101 to the patient's skin without the need to drill or form additional holes through microneedle 130.

Figure 23:
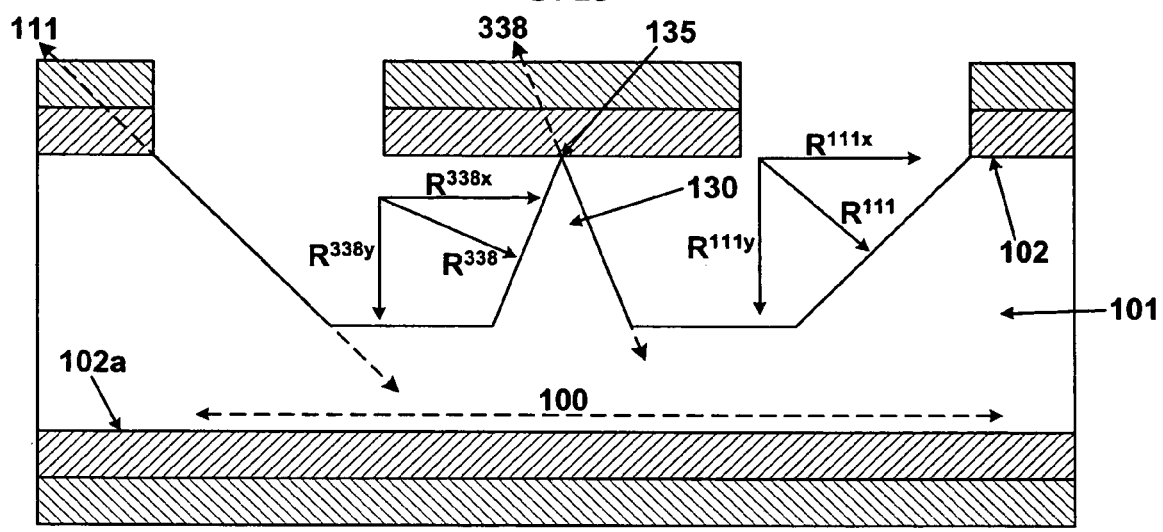
FIG. 23 is an illustration of the vector components of the anisotropic etching according to an embodiment of the invention.

FIG. 23 illustrates the vector components utilized during the step of anisotropically etching the body of the one or more microneedles 130 from the substrate 101. In particular, the anisotropic etch is made based on three components of etching, a horizontal component, a vertical component, and an angled component. The horizontal component, or X-component, runs horizontally, parallel to plane 100, which is the plane of the front surface 102 and the rear surface 102a of the substrate 101. The vertical component, or Y-component, runs vertically, in a manner perpendicular to the 100 plane. The angled component runs in a direction perpendicular to the surface being etched. For example, if the surface being etched is a horizontal surface, for example, the front surface 102 of the substrate 101, the angled component would have the same magnitude as the Y-component, and the X-component would have a magnitude of zero. Similarly, if the surface being etched is a vertical surface, the angled component would have the same magnitude as the X-component, and the Y-component would have a magnitude of zero.

The anisotropic etching of the microneedle 130 preferably involves three separate etching planes. The first plane is the plane 100, which is the horizontal plane of the front surface 102 of the substrate 101. The second plane is the plane 338, which is an angled plane running parallel to the outer surfaces 132 of the microneedles 130. The third plane is the plane 111, which is an angled plane running parallel to the surface of the wall 140. With respect to the etching of plane 100, the etch occurs only in a downward direction. This is because there is no horizontal vector component to the etchant.

With respect to the etching of plane 338, the etch has both horizontal and vertical vector components. In particular, the direction of the etch, $R^{338}$, is perpendicular to the plane 338 to be etch. Since $R^{338}$ is an angled direction of etching, there is a Y-component, $R^{338y}$, and an X-component, $R^{338x}$. The $R^{338x}$ component etches the surface of the microneedle 130 in a horizontal manner and the $R^{338y}$ component etches the surface of the microneedle 130 in vertical manner. In addition, the etching components are applied on all side of microneedles 130, and the speed of etching is virtually identical on all sides. In this manner, the etching of microneedle continues until the tip 135 of microneedle 130 no longer touches protective layers 105 and 110. During this step, the anisotropic etchant undercuts the mask formed by the remaining protective layers, and removes the portion of the substrate around the area where microneedle is formed. After the undercut is complete, the remaining structure is a sharp tip bounded by 338 plane. Thus, microneedle 130 achieves a sharp tip at tip 135, the sharpness of which is directly proportional to the slope of plane 338. By etching microneedle 130 in this manner, the duration of the etch is not critical to the sharpness of microneedle 130 because after a sharp tip is achieved, further etching will not affect tip sharpness, as the angle of plane 338 will remain constant throughout the etching process. For example, if the duration of the etch is larger than expected, the height $H_{130}$ of the microneedles 130 will be reduced, but the tip will remain sharp.

With respect to the etching of plane 111, the etch also has both horizontal and vertical vector components. In particular, the direction of the etch, $R^{111}$, is perpendicular to the plane 111 to be etch. Since $R^{111}$ is an angled direction of etching, there is a Y-component, $R^{111y}$, and an X-component, $R^{111x}$. The $R^{111x}$ component etches the surface of the microneedle 130 in a horizontal manner and the $R^{111y}$ component etches the surface of the microneedle 130 in vertical manner. The duration of the etch of plane 111 is not critical.

Thus, the anisotropic etching of substrate 101 to form microneedles 130 is conducted such that fast etching secondary planes 111 and 338 are exposed, which results in an etching effect exceeds the ordinary etch rate of the plane 100. This results in an atomically sharp tip 135 for microneedle 130 which remains sharp after the protective layer is fully undercut regardless of the overetch time. If etching conditions meet requirements of the critical anisotropy ratio, i.e. the vertical effect of the wall etch rate exceeds the surface etching rate, arbitrary tip heights from the floor and recess distances from the original surface could be obtained once values can be established for etch rates of relevant crystallographic planes. Similar effect are observed in silicon wafers for appropriate etch pattern alignment to crystallographic planes.

One aspect of the uniqueness of the process involved in fabrication of microneedles as described herein lies in the fact that microneedle sharpness is not dependent on how precisely the etch process is timed, or any other processing parameter. Instead, microneedles fabricated by the process of this invention are "shelf-sharpening". Due to the fact that the etch rate of plane 338 is faster than the etch rate of the plane 100, even if the etch time is longer than needed to completely undercut the protective layers above the microneedle, the sharpness of the microneedle is not compromised. If an overetch occurs, the body of the microneedle starts to "move downwards". For example, the height of the microneedle decreases, and if the overetch occurs for a long enough period of time, the microneedle will essentially disappear. However, because the rate at which the microneedles move down after the undercut is complete is slower than the rate of undercut, it is possible to control the microneedle height within an acceptable range of error, assuming optimized processing conditions.

Microneedle height and array arrangements are highly flexible and only require a change in mask layout. Etch time is the only specific parameter that is adjusted for different height microneedles. The spacing between adjacent microneedles corresponds to the final microneedle base width, therefore the real estate that is not being used as an active device area is minimal. Delivery of a sufficient amount of drug can be achieved by providing a denser array of microneedles, as well as by providing a longer microneedle. This leaves a high level of flexibility in terms of device design, real estate on the silicon wafer, and ultimately a low cost per single microneedle array die.

Mechanical robustness of the microneedle structure described herein is superior to any silicon based microneedle known in the art. The microneedles described herein have a microneedle height to width aspect ratio of, for example 1:1.5, and the structure is predominantly solid, rather that hollow. These factors contribute to the force required to penetrate human skin being smaller than that required to break the penetrating elements. This applies to both single microneedles and various microneedle arrays, for which penetration forces are different depending on the number of penetrating elements, their height and spacing between adjacent microneedles.

Figure 24:
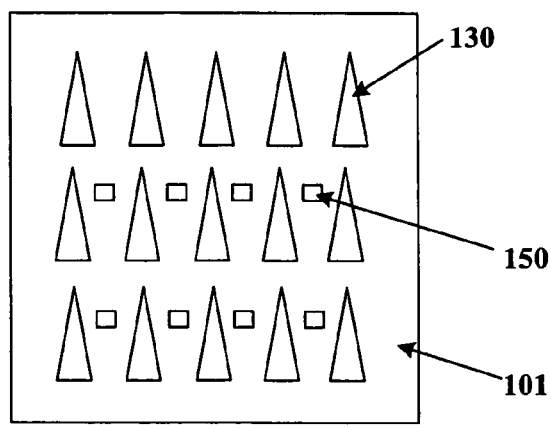
FIG. 24 shows an array of microneedles on a substrate with through-holes according to an embodiment of the invention.

FIG. 24 shows a microneedle array formed by the method described with reference to FIGS. 1-7 above. The microneedle array comprises a substrate 101 in which a plurality of microneedles 130 are formed. In addition, a plurality of through-holes 150 are formed in the substrate 101 to allow the transfer of substances from the back side of the substrate to the front side of the substrate. The number of microneedles 130 and their specific geometry and size may vary. These criteria are determined based on a particular substance and the amount of that substance to be delivered to a patient over a period of time. The microneedle array penetrates the patient's skin by means of an applied pressure from the back side of the array.

Moreover, the microneedles may be coated with one or more substances to be administered to a patient through the skin. Preferably, at least one of the substances to be administered to the patient is incorporated into a polymeric material.

Many polymers and polymeric materials are suitable for medical coatings. Generally, any polymer, whether water-soluble (hydrophilic), or water-insoluble (hydrophobic) can be used to create a coating as long as the polymer is of sufficiently high molecular weight to form continuous films of sufficient mechanical strength, can be created from a monomer by a vacuum deposition technique, or can be created by a heat or light induced polymerization reaction.

Therefore, many polymers can be considered as a coating material and those knowledgeable in the art know of hundreds of different coating materials and many different ways to apply a coating. A brief overview of medical coatings is provided in "Chapter 9 of the Handbook of Materials for Medical Devices, edited by J. R. Davis, published in 2003 by ASM International, Materials Park, Ohio, 44073.

The use of a vapor deposition technique to create a coating can be illustrated by the Parylene Coating Process. In this process, the starting material is diparaxylylene which is converted into a polymer film during the vacuum deposition process.

An alternative approach consists of applying a solution of low-molecular weight substances (monomers) to a surface. The solution also preferably contains a suitable additive, capable of initiating a polymerization reaction upon heating or upon exposure to visible or UV light. In this case, a polymer is formed after the solution is applied to the surface to be coated. Upon evaporation of the solvent, the polymer formed during the polymerization reaction remains behind in the form of a thin film covering the surface. If a pharmaceutically active agent was admixed into the coating solution, the active agent becomes entrapped within the polymer coating and can be released from the coating over time.

When using a spray coating, dip coating, or solvent casting procedure to fabricate the coating, the polymer should be soluble in at least one solvent so that a polymer solution can be prepared. Upon evaporation of the solvent, the initially dissolved polymer remains behind as thin film covering the surface to which the polymer solution was applied. If the polymer is water soluble (hydrophilic), an aqueous medium can be used as the coating solution. If the polymer is water-insoluble (hydrophobic), a low-boiling organic solvent, or a mixture of solvents) such as alcohol, tetrahydrofuran, methylene chloride can be used to create the coating solution. A pharmacologically active agent may also be dissolved within the coating solution.

According to an embodiment of the invention, it is desirable that the coating release an active agent over a given period of time. Such active agents can be flavoring moieties, fragrances, or pharmacologically active drug molecules. In this case, the coating must permit the release of the active agent, either by slow diffusion through the coating, by dissolution of the coating upon contact with an aqueous medium, or by degradation (erosion) of the coating upon contact with an aqueous solution. It is possible for all three mechanisms of active agent release to operate concomitantly.

As outlined above, such "active agent releasing coatings" can be obtained by applying a coating solution containing the active agent, monomers, and moieties capable of initiating a polymerization reaction upon exposure to heat or light.

Such coatings can also be obtained by applying an aqueous coating solution containing a hydrophilic (water soluble) polymer and the active agent. Upon evaporation of the water, a water-soluble polymer coating may be obtained that contains the active agent. When the coated surface comes in contact with moist human tissue, the water-soluble coating will dissolve, releasing the entrapped active agent.

Such coatings can also be obtained by applying a solution containing a hydrophobic polymer (or a mixture of polymers) and an active agent dissolved in a suitable organic solvent (or solvents). Upon evaporation of the organic solvent(s), a water-insoluble polymer coating may be obtained that contains the active agent. When the coated surface comes in contact with moist human tissue, the entrapped active agent can be released by diffusion through the polymer coating, or, in the case of a biodegradable polymer, the entrapped active agent can be released upon degradation of the polymeric coating.

Irrespective of the mode in which the coating is applied, the following characteristics are desirable for the materials used in the coating for medical devices or drug delivery systems.

First, the materials used in the coating should be biocompatible. Coatings should to exhibit long-term compatibility and a nonreactive relationship with body fluids and tissues. The coating should not undergo any significant chemical interaction with the substrate to which it is being applied, nor should it produce any toxic by-products or extracts that could be harmful to a patient or to the function of the item being coated.

In addition, the materials used in the coating should be inert. The materials used in the coating should not contaminate the substrate with outgassing or with by-products from catalysts, cure agents, solvents, or plasticizers.

Furthermore, the materials used in the coating should be conformable. The coating should offer conformability to highly variable surface geometries, and should provide effective isolation of all surfaces, including hidden areas, crevices, etc., without bridging or pooling. The coating should also be able to maintain conformability at all magnitudes of substrate and surface feature sizes, from macro to micro.

Moreover, the materials used in the coating should have a specific finished thickness. The coating may need to meet extremely tight dimensional tolerances, and therefore be quite thin, while at the same time be able to provide uncompromised physical, chemical, or electrical protection for the substrate with coverage that is free of voids and pinholes. Thus, the finished thickness of the coating is important.

In addition, the materials used in the coating should be able to withstand a significant amount of loading. A coating often needs to function dependably, even in the presence of a high payload of an active agent (drug) that is entrapped within the coating.

Similarly, the materials used in the coating should be resistant to flaking and delamination. It is preferable that a coating have considerable flaking resistance. It should also be sufficiently robust and adherent to prevent flaking/delamination from the coated surface or from itself.

Furthermore, the materials used in the coating should be able to be sterilized. When being used in medical devices, a coating should be capable of withstanding the effects of one or more sterilization processes.

Accordingly, the following materials may be used as the preferred drug-releasing, medical coatings for the microneedle array described herein.

First, hydrophilic polymers may be used which can be applied while dissolved in a aqueous coating solution together with an active agent. If provided in sufficiently high molecular weight (usually over 50,000) upon drying of the aqueous coating solution, these materials can form a thin film coating entrapping the active agent. When the coatings come in contact with moist tissues, the coatings dissolve within hours to days, releasing any entrapped active agent. Table 1 below provides an exemplary listing of suitable hydrophilic polymers that can be considered for use in water-soluble, medical coatings, and is not comprehensive. The art of using hydrophilic polymer coatings for medical devices is more fully described in "Hydrophilic Polymer Coatings For Medical Devices: Structure/Properties, Development, Manufacture and Applications by Richard J. LaPorte, published by Technomic Publishers, Lancaster, Pa. in 1997).

TABLE 1

Suitable Hydrophilic Polymers for Use in Water-Soluble Medical Coatings

Polyacrylamide
Poly(Acrylic Acid-Co-Hypophosphite)
Polyacrylic Acid, Sodium Salt
Poly(Alkyl(C16–22)Acrylate)
Poly(Ethylene Glycol)
Poly(Propylene Glycol)
Poly(Vinyl Alcohol)
Polypyrrolidone
Polyvinylpyrrolidone
Polysaccharides Such As Chitosan, Alginate, Amylose
Water Soluble Fractions Of Proteins Such As Collagen, Gelatin In addition, the exemplary biostable, hydrophobic polymers listed in Table 2 below may be used. These non-biodegradable, hydrophobic polymers should be dissolved in organic solvents to be applied as a coating. The polymers listed here are non-degradable, e.g., the active agent entrapped within the coating can only be released by diffusion through the polymeric coating. If provided with sufficiently high molecular weight, each of the listed polymers will form a thin film coating upon evaporation of the coating solvent(s). Several of the polymers listed represent polymer families comprising of a wide range of individual compositions, and the list in Table 2 is not comprehensive.

TABLE 2

Suitable Biostable, Hydrophobic Polymers for Use in Medical Coatings

Poly(Divinylbenzene-Co-Ethylstyrene)
Polyisobutylene
Polylimonene
Polymaleic Acid
Polyoxyethylene Dioleate
Poly(Vinyl Acetate)
Poly(Vinyl Chloride)
Polystyrene
Polyurethane
Polyurethane-Poly(Ethylene Oxide) Graft Copolymer
Poly(Ether Urethane)
Poly(Ether Urethane Urea)
Polyethylene
Polycarbonate
Poly(Ester Amide)
Polyacrylonitrile
Poly(Aryl Ether Keton)
Poly(Dimethyl Siloxane) And Other Polysiloxanes
Poly(Ethylene Terephthalate) And Other Polyesters
Poly(2-Hydroxyethylmethacrylate)
Polymethylmethacrylate In addition, the exemplary biodegradable, hydrophobic polymers listed in Table 3 below may be used in the present invention. The listed polymers include biodegradable, hydrophobic polymers which should to be dissolved in organic solvents to be applied as a coating. Pharmaceutically active agents can also be mixed into the coating solution. After drying of the solvent, each of the listed polymers can form a thin film coating, thereby entrapping the active agent. Upon exposure to moist tissue, the active agent will be released due to diffusion from the coating and/or hydrolytic degradation of the polymer coating.

TABLE 3

Suitable Biodegradable, Hydrophobic Polymers for Use in Medical Coatings

Poly(Glycolic Acid), Poly(Lactic Acid) And Co-Polymers Thereof
Polyhydroxybutyrate (Phb)
Polyhydroxyvalerate (Phv), And Co-Polymers Thereof
Polycaprolactone
Polydioxanone
And Other Synthetic Degradable Polyesters, Blends, Thereof,
And Copolymers Thereof
Polyanhydrides
Poly(Amino Acids) Such As Poly(Benzyl Glutamate)
"Pseudo"-Poly(Amino Acids)
Such As Tyrosine-Derived Polycarbonates And Polyarylates
And Copolymers Thereof With Poly(Ethylen Glycol)
Poly(Ortho Ester)
Polyphosphazenes
Poly(Propylene Fumarate)

The polymer coating process may be performed on a wafer or a die level. After the microneedles penetrate the patient's skin, the microneedle array may be left inside the skin for a required period of time, which allows the polymer coating to completely release and remain inside the patient's body after the microneedles are removed. This results in a controlled release of drug into the circulation over an extended period of time, while the time of residence of the microneedles inside the skin is minimized. Any suitable coating method may be used.

Thus, an embodiment of the invention provides a drug delivery device comprising a substrate having a back surface and a front surface, one or more microneedles extending upwards from the front surface of the substrate, the microneedles having a generally conical-shaped body defined by a plurality of surfaces sloping upwards from a relatively broad base to a tip, and one or more substances coating the microneedles, the one or more substances being operable to be administered to a patient, wherein the tips of the one or more microneedles are sufficiently sharp to penetrate an outer layer of the skin of the patient. In addition, these substances may be incorporated into a polymeric material.

When the substances are incorporated into a polymeric material, the device comprises a plurality of polymer-drug coated microneedles extending from a substrate. When administered to a patient, pressure is applied to the back surface of the microneedle array to cause the microneedles to penetrate the stratum corneum of the patient and to produce local and/or systemic, physiological and/or pharmacological effect. As described above, the microneedle array may include one or more through-holes on the substrate to facilitate transfer of one or more substances from the back surface of the substrate to the front surface of the substrate.

When a polymer-based coating is used, the delivery of substances, for example, drugs, is primarily facilitated via the polymer based coating that incorporates one or more substances to be delivered, and can optionally be combined with fluidic transfer of one or more substances through multiple through-holes. This device is designed for high volume production using semiconductor processing techniques at high volume and low cost, therefore it has an enormous economical impact.

In addition, an embodiment of the invention relates to a method of administering one or more substances to a patient comprising the steps of penetrating at least an outer layer of the skin of the patient with one or more microneedles extending from a front surface of a substrate, at least one of the microneedles being coated with one or more substances to be administered to the patient, and releasing at least one of the substances into the patient, wherein the microneedles have a generally conical-shaped body defined by a plurality of surfaces sloping upwards from a relatively broad base to a tip.

In addition to the steps described above, when administering a substance to a patient with the microneedle array of the invention, the microneedle array may be rubbed against the outer layer of the patient's skin to abrade the skin prior to penetration. This abrasion facilitates penetration and creates an abraded portion of the skin which may be more receptive to receive the substances to be delivered.

Figure 25:
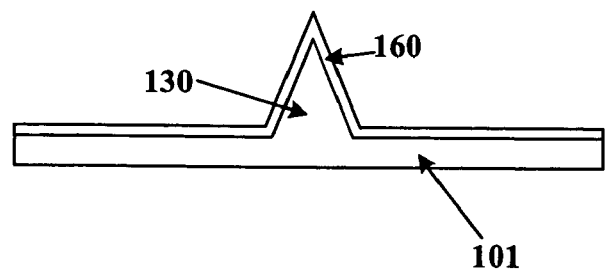
FIG. 25 shows the substrate of FIG. 6 having a coating of one or more substances according to an embodiment of the invention.
Figure 26:
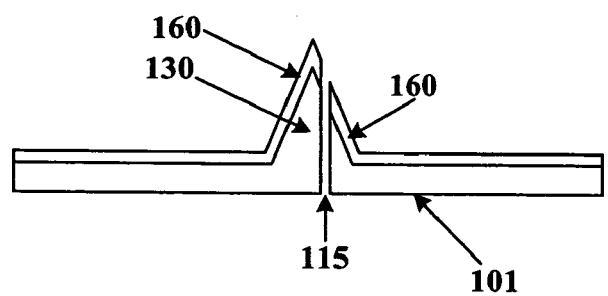
FIG. 26 shows the substrate of FIG. 13 having a coating of one or more substances according to an embodiment of the invention.
Figure 27:
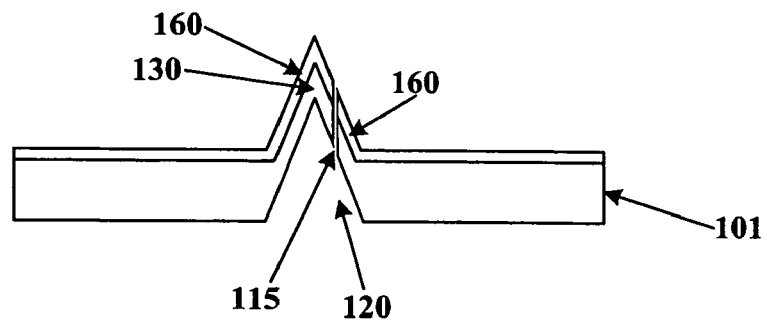
FIG. 27 shows the substrate of FIG. 21 having a coating of one or more substances according to an embodiment of the invention.

As described above and shown in FIGS. 25-27, the one or more microneedles may be coated with one or more substances 160 to be delivered to a patient. These substances may be incorporated into a polymeric material. In addition, the one or more substance may be time released substances, thereby allowing for the release of the substances into the patient's body over an extended period of time. When the substances coating the microneedles are time-release substances, the microneedles may be left in the patient's body for a sufficient period of time to allow the substances to be released into the patient.

Figure 28:
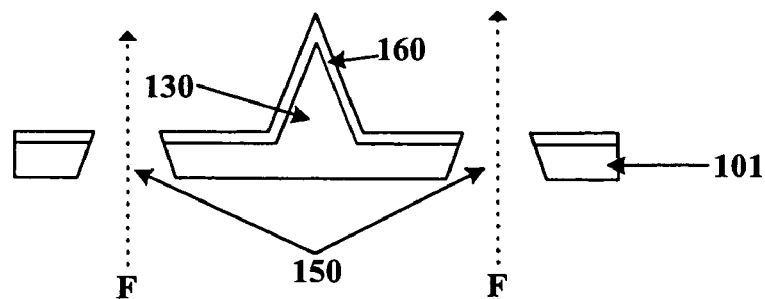
FIG. 28 shows the substrate of FIG. 7 having a coating of one or more substances according to an embodiment of the invention wherein the direction of transfer of one or more additional substances is shown.
Figure 29:
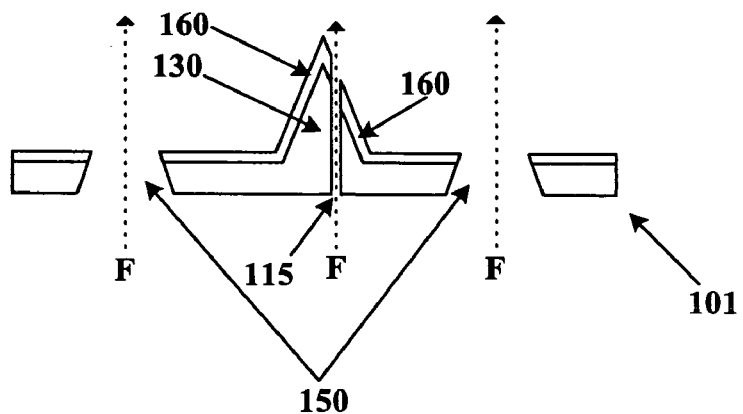
FIG. 29 shows the substrate of FIG. 14 having a coating of one or more substances according to an embodiment of the invention wherein the direction of transfer of one or more additional substances is shown.
Figure 30:
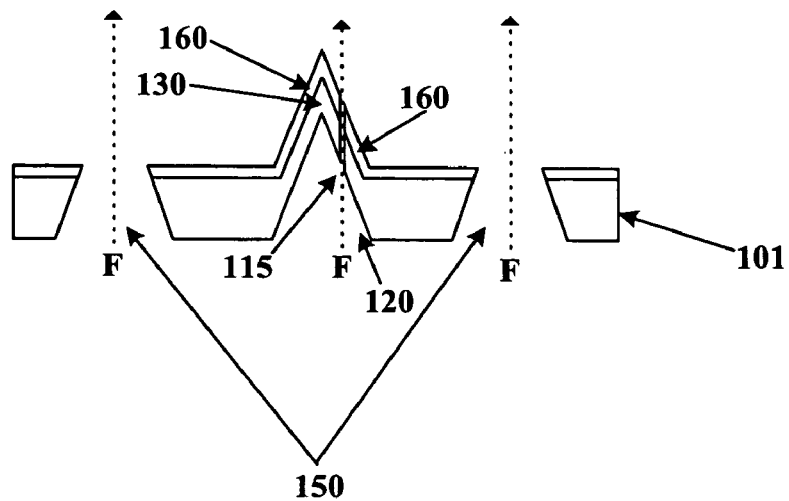
FIG. 30 shows the substrate of FIG. 22 having a coating of one or more substances according to an embodiment of the invention wherein the direction of transfer of one or more additional substances is shown.

In addition, as is shown in FIGS. 28-30, additional substances may be administered to the patient from the back surface of the substrate to the front surface of the substrate through one or more holes that extend from the back surface of the substrate to the front surface of the substrate. In this manner, substances are transferred through the hole in the substrate to the patient along the path F. Similarly, additional substances may be transferred from the back surface of the substrate to the patient via one or more holes that extend from the back surface of the substrate to at least one of the surfaces of the one or more microneedles. These holes allow substances to be administered from the back surface of the substrate directly to the patient through the surfaces of the microneedles, as is indicated by path F in FIGS. 29-30.

In addition, FIGS. 31-37 show an embodiment of the invention wherein an offset 126 is formed in the substrate 101. The offset 126 is used to partially remove the microneedles after penetration to allow the flow of the substance being administered into the skin. In this regard, the offset creates spacing between the outer layer of the patient's skin and the surface of the microneedle array. Moreover, the use of an offset can allow the depth of the penetration to be controlled.

Figure 31:
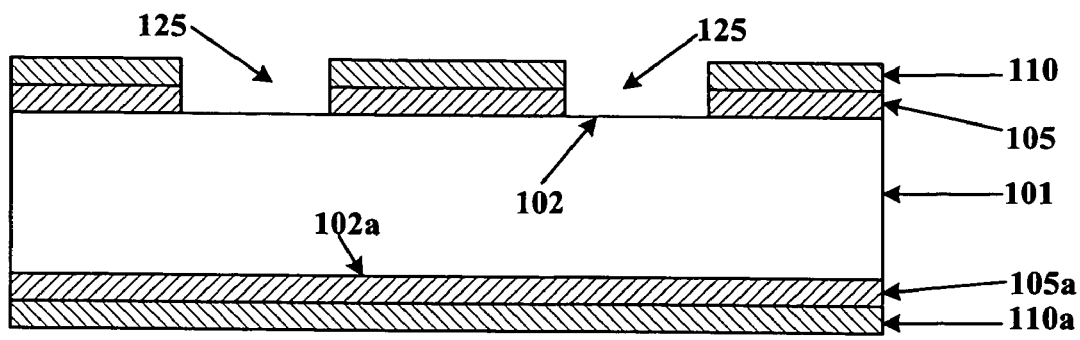
FIG. 31 shows an embodiment of the invention wherein two protective layers on a substrate have been etched to form a mask.
Figure 32:
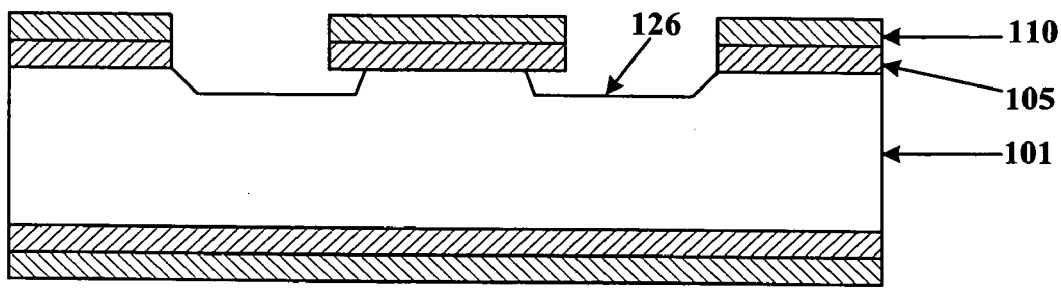
FIG. 32 shows the substrate of FIG. 31 after a first portion of the substrate is etched according to an embodiment of the invention.
Figure 33:
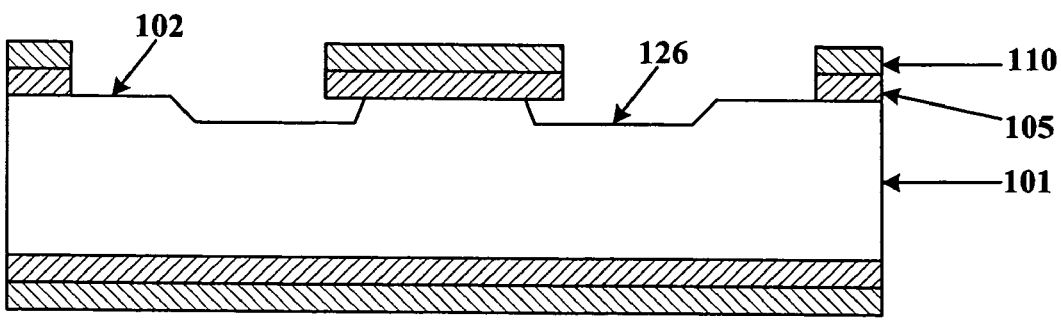
FIG. 33 shows the substrate of FIG. 32 wherein the protective layers have been further etched to define an offset portion of the substrate.
Figure 34:
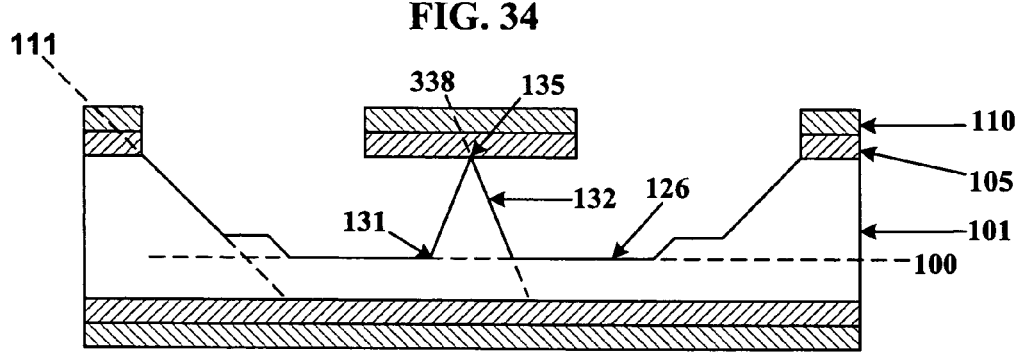
FIG. 34 shows the substrate of FIG. 33. after the substrate is further etched to form a microneedle according to an embodiment of the invention.
Figure 35:
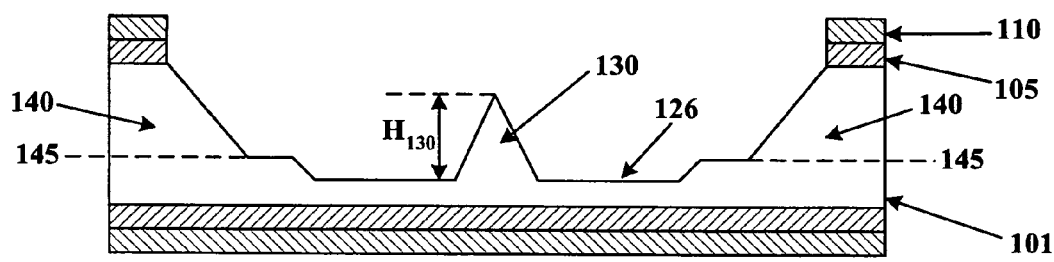
FIG. 35 shows the substrate of FIG. 34 after the etching is complete and the microneedle is formed according to an embodiment of the invention.
Figure 36:
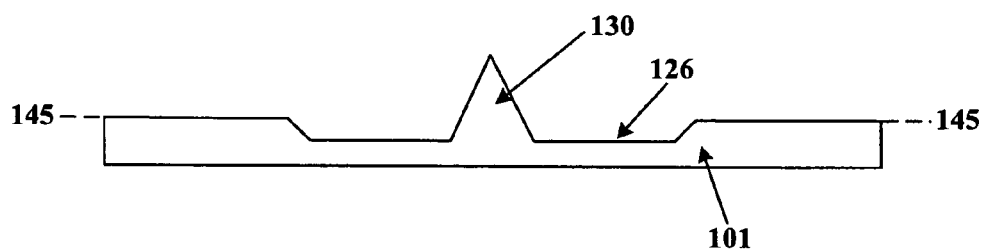
FIG. 36 shows the substrate of FIG. 35 with the microneedle extending upwards from the substrate according to an embodiment of the invention.
Figure 37:
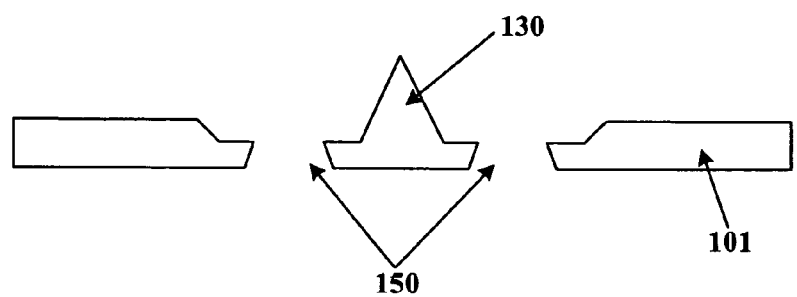
FIG. 37 shows the substrate of FIG. 36 wherein the substrate has through-holes extending from the back surface of the substrate to the front surface of the substrate according to an embodiment of the invention.
Figure 38:
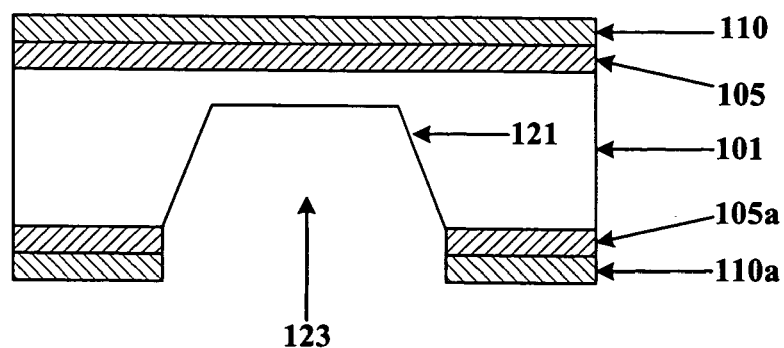
FIG. 38 shows a cross-sectional front view of an embodiment of the invention wherein protective layers have been grown or deposited on a substrate and a lateral groove has been etched into the back surface of the substrate.
Figure 39:
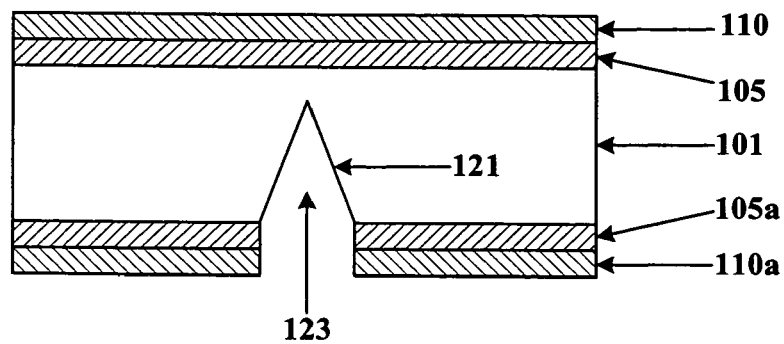
FIG. 39 shows a cross-sectional side view of the embodiment shown in FIG. 38.
Figure 40:
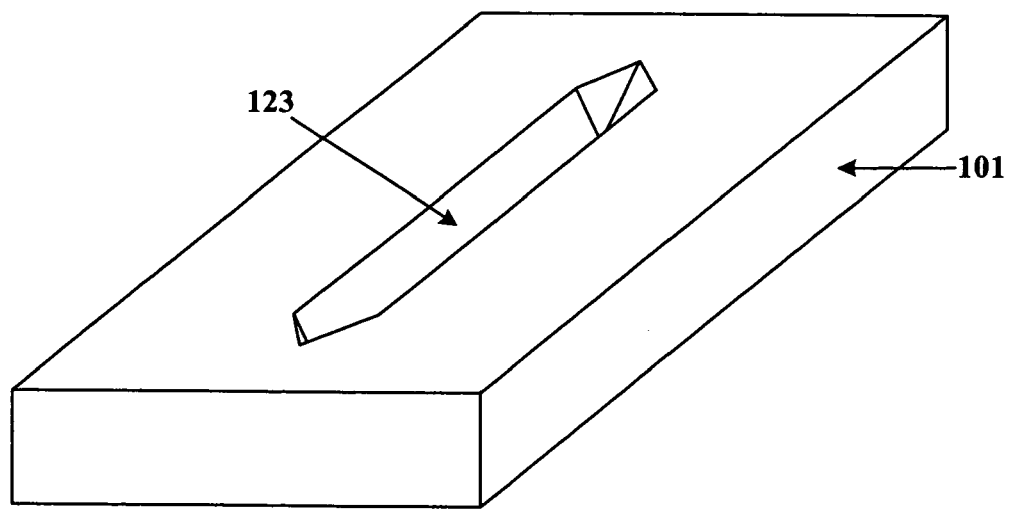
FIG. 40 shows a perspective view of the substrate after the lateral groove shown in FIGS. 38-39 has been formed.

The method for fabricating the microneedle 130 and offset 126 shown in FIGS. 31-37 is substantially similar to the methods described above with reference to FIGS. 1-22. However, in this embodiment, to form the offset portion, protective layers 110 and 105 are etched more than once, with an intermediate anisotropic etching step. As shown in FIG. 31, protective layers 110 and 105 are first etched to create a mask for etching the surface 102 of substrate 101. Then, as is shown in FIG. 32, a portion of substrate 101 is anisotropically etched through the mask to create offset 126, defining a recessed portion of the substrate. Next, as is shown in FIG. 33, protective layers 110 and 105 may be further etched to increase the portion of surface 102 of substrate 101 that is exposed, thereby defining the extent of the offset (i.e. the depth of the recessed portion). It is important to note that protective 110 may be etched to define the offset prior to the first anisotropic etching step.

Next, the anisotropic etch of substrate 101 is continued to form the body of microneedle 130, with the offset 126 being maintained in substrate 101 as the etching continues. The depth and width of the offset can be specified by controlling the duration of the anisotropic etch prior to the second etching of the protective layers.

What is claimed is:

1. A method of fabricating a microneedle array in a substrate having a front surface and a back surface, comprising:
   forming one or more protective layers on the front surface of the substrate;
   applying photoresist to the one or more protective layers on the front surface of the substrate;
   removing at least a portion of the one or more protective layers from the front surface of the substrate;
   removing the photoresist from the front surface of the substrate;
   anisotropically etching the front surface of the substrate to form one or more microneedles in the substrate, said microneedles having a conical-shaped body defined by a plurality of surfaces sloping upwardly from a base to a tip;
   forming one or more protective layers on the back surface of the substrate;
   applying photoresist to the one or more protective layers on the back surface of the substrate;
   removing a least a portion of the one or more protective layers from the back surface of the substrate;
   removing the photoresist from the back surface of the substrate; and
   etching anisotropically one or more conical holes in the substrate such that at least one of the conical holes extends from the back surface of the substrate into the body of the one or more microneedles, wherein the conical holes have a plurality of internal surfaces formed by the etching;
   wherein the bases of the one or more microneedles are formed integrally with the substrate and the tips of the one or more microneedles are capable of penetrating an outer layer of the skin of a patient.

2. The method of claim 1 wherein the substrate is comprised of a silicon wafer.

3. The method of claim 1 wherein the step of forming one or more protective layers on the front surface of the substrate comprises forming at least one oxide layer.

4. The method of claim 1 wherein the step of forming one or more protective layers on the front surface of the substrate comprises forming at least one silicon nitride layer.

5. The method of claim 1 wherein the step of removing at least a portion of the one or more protective layers from the front surface of the substrate comprises the step of performing photolithography on the front surface of the substrate to form a footprint for the microneedle array.

6. The method of claim 1 wherein the step of removing at least a portion of the one or more protective layers from the front surface of the substrate comprises the step of etching the one or more protective layers using reactive ion etching.

7. The method of claim 1 wherein the step of anisotropically etching the front surface of the substrate to form the one or more microneedles comprises etching the substrate using KOH etching.

8. The method of claim 1 wherein the step of anisotropically etching the front surface of the substrate to form the one or more microneedles comprises etching the front surface of the substrate using TMAH etching.

9. The method of claim 1, and further comprising removing the one or more protective layers from the front surface of the substrate.

10. The method of claim 1, and further comprising removing at least a portion of the substrate located above the surface of the substrate immediately adjacent to the bases of the one or more microneedles.

11. The method of claim 1, and further comprising forming one or more holes in the substrate that extend from the back surface of the substrate to the front surface of the substrate.

12. The method of claim 1 wherein the step of forming one or more conical holes on the back surface of the substrate comprises forming one or more conical holes that extend from the back surface of the substrate to at least one of the surfaces of the one or more microneedles.

13. The method of claim 1, and further comprising forming one or more holes through the substrate extending from at least one of the surfaces of the one or more conical holes to the surfaces of the one or more microneedles.

14. The method of claim 1 wherein the step of forming one or more protective layers on the back surface of the substrate comprises forming at least one oxide layer on the back surface of the substrate.

15. The method of claim 1 wherein the step of forming one or more protective layers on the back surface of the substrate comprises forming at least one silicon nitride layer on the back surface of the substrate.

16. The method of claim 1 wherein the step of removing at least a portion of the one or more protective layers on the back surface of the substrate comprises etching the one or more protective layers on the back surface of the substrate using reactive ion etching.

17. The method of claim 1 wherein the step of etching the back surface of the substrate comprises etching the back surface of the substrate using KOH etching.

18. The method of claim 1 wherein the step of etching the back surface of the substrate comprises etching the back surface of the substrate using TMAH etching.

19. The method of claim 1, and further comprising removing the one or more protective layers from the back surface of the substrate.

20. The method of claim 1 wherein the step of etching the back surface of the substrate to form one or more holes comprises etching a lateral groove in the substrate such that the tip of the lateral groove extends from the back surface of the substrate into the body of one or more microneedles, thereby creating at least one opening on the surface of the microneedle.

21. The method of claim 1, and further comprising coating at least one of the microneedles with one or more substances to be administered to a patient through the skin.

22. The method of claim 21 wherein at least one of the substances to be administered to the patient is incorporated into a polymeric material.

23. A method of fabricating a microneedle array in a substrate having a front surface and a back surface, comprising:
    forming one or more protective layers on the front surface of the substrate;
    removing at least a portion of the one or more protective layers from the front surface of the substrate;
    etching anisotropically the front surface of the substrate to form an offset portion in the substrate;
    removing an additional portion of at least one or more protective layers;
    etching anisotropically the front surface of the substrate to form one or more microneedles in the substrate, wherein the microneedles have a conical-shaped body defined by a plurality of surfaces sloping upwardly from a base to a tip;
    forming one or more protective layers on the back surface of the substrate;
    applying photoresist to the one or more protective layers on the back surface of the substrate;
    removing at least a portion of the one or more protective layers from the back surface of the substrate;
    removing the photoresist; and
    etching anisotropically one or more conical holes in the back surface of the substrate corresponding to a position of at least one of the microneedles such that at least one of the conical holes extends from the back surface of the substrate into the body of the one or more microneedles, wherein the conical holes have a plurality of internal surfaces formed by the etching, and
    wherein the bases of the one or more microneedles are formed integrally with the substrate and the tips of the one or more microneedles are capable of penetrating an outer layer of the skin of a patient.

24. The method of claim 23 wherein the substrate is comprised of a silicon wafer.

25. The method of claim 23 wherein the step of forming one or more protective layers on the front surface of the substrate comprises forming at least one oxide layer.

26. The method of claim 23 wherein the step of forming one or more protective layers on the front surface of the substrate comprises forming at least one silicon nitride layer.

27. The method of claim 23 wherein the step of removing at least a portion of the one or more protective layers from the front surface of the substrate comprises the step of performing photolithography on the front surface of the substrate to form a footprint for the microneedle array.

28. The method of claim 23 wherein the step of removing at least a portion of the one or more protective layers from the front surface of the substrate comprises the step of etching the one or more protective layers using reactive ion etching.

29. The method of claim 23 wherein the step of anisotropically etching the front surface of the substrate to form the one or more microneedles comprises etching the front surface of the substrate using KOH etching.

30. The method of claim 23 wherein the step of anisotropically etching the front surface of the substrate to form the one or more microneedles comprises etching the front surface of the substrate using TMAH etching.

31. The method of claim 23, and further comprising removing the one or more protective layers from the front surface of the substrate.

32. The method of claim 23, and further comprising removing at least a portion of the substrate located above the surface of the substrate immediately adjacent to the bases of the one or more microneedles.

33. The method of claim 23 wherein the step of forming one or more holes on the back surface of the substrate comprises forming one or more holes that extend from the back surface of the substrate to at least one of the surfaces of the one or more microneedles.

34. The method of claim 23, and further comprising forming one or more holes through the substrate extending from at least one of the surfaces of the one or more conical holes to the surfaces of the one or more microneedles.

35. The method of claim 23 wherein the step of forming one or more protective layers on the back surface of the substrate comprises forming at least one oxide layer.

36. The method of claim 23 wherein the step of forming one or more protective layers on the back surface of the substrate comprises forming at least one silicon nitride layer.

37. The method of claim 23 wherein the step of removing at least a portion of the one or more protective layers on the back surface of the substrate comprises etching the one or more protective layers on the back surface of the substrate using reactive ion etching.

38. The method of claim 23 wherein the step of etching the back surface of the substrate comprises etching the back surface of the substrate using KOH etching.

39. The method of claim 23 wherein the step of etching the back surface of the substrate comprises etching the back surface of the substrate using TMAH etching.

40. The method of claim 23, and further comprising removing the one or more protective layers from the back surface of the substrate.

41. The method of claim 23 wherein the step of etching the back surface of the substrate to form one or more holes comprises etching a lateral groove in the substrate such that the tip of the lateral groove extends from the back surface of the substrate into the body of one or more microneedles, thereby creating at least one opening on the surface of the microneedle.

42. The method of claim 23 and further comprising coating at least one of the microneedles with one or more substances to be administered to a patient through the skin.

43. The method of claim 42 wherein at least one of the substances to be administered to the patient is incorporated into a polymeric material.

* * * * *